Feb. 1, 1966 R. BENNETT Plant Pat. 2,596
AZALEA PLANT
Filed Nov. 25, 1964
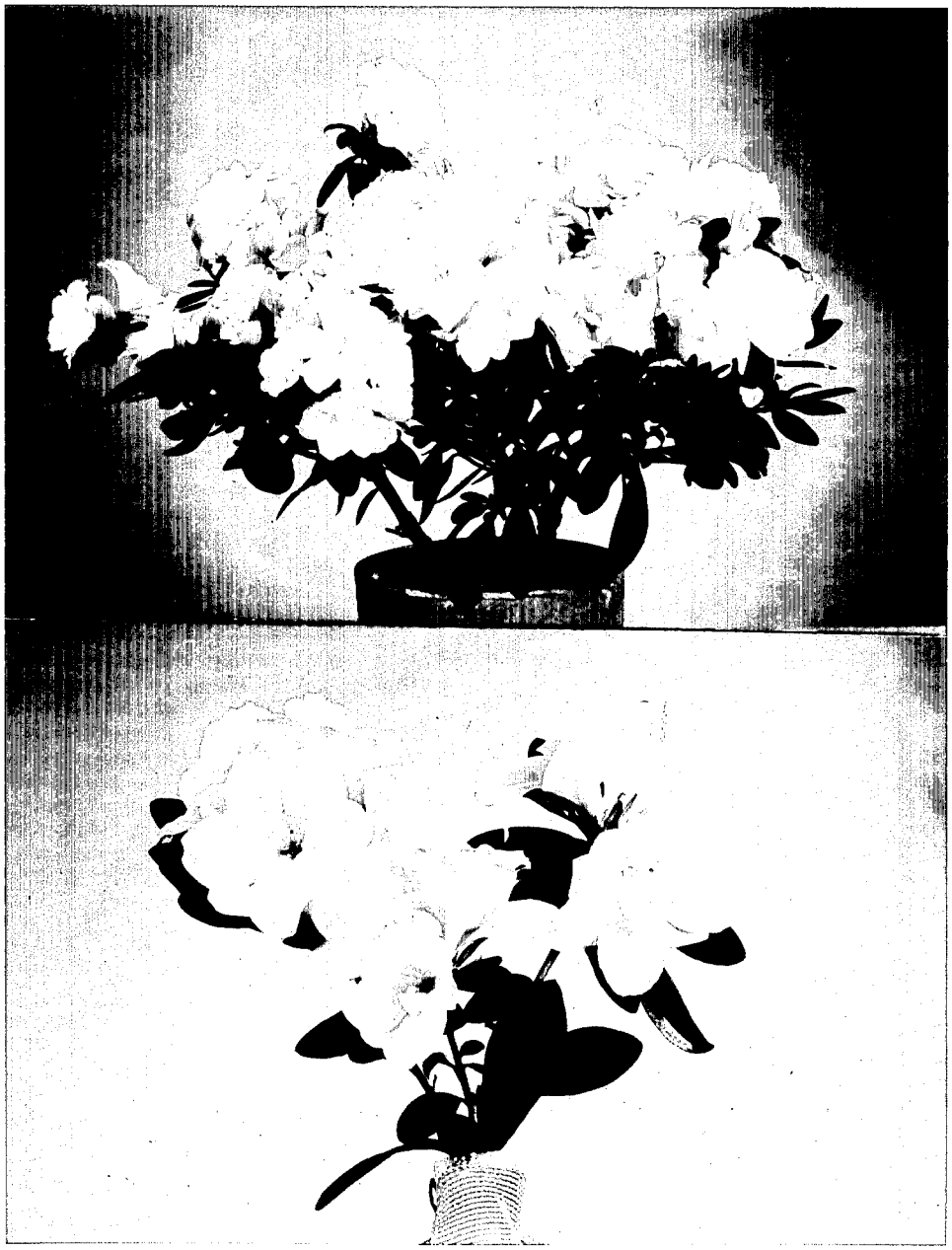
Inventor.
Richard Bennett
By: Robbs & Robb
Attorneys.

United States Patent Office

Plant Pat. 2,596

Patented Feb. 1, 1966

2,596

AZALEA PLANT

Richard Bennett, Guthrie, Okla., assignor to Furrow & Company, Inc., Oklahoma City, Okla., a corporation of Oklahoma Filed Nov. 25, 1964, Ser. No. 414,039
1 Claim. (Cl. Plt.—55)

The present invention relates to a new and distinct variety of azalea plant which was discovered by me in the greenhouses of my employer-assignee, at Guthrie, Oklahoma, as a sport of the azalea variety known as "Gloria" (unpatented).

At the time of my discovery aforementioned, I was tending a block of several hundred plants of the variety "Gloria" which were being grown commercially under my care in a greenhouse on the nursery property of my employer-assignee, and in the course of my duties, my attention was attracted to one particular plant amongst this block which bore several white flowers, instead of the usual pink flowers which are normal for the variety "Gloria." Upon close inspection of this plant, I found that it had sported, and I thereupon took prompt steps to preserve the sport so that it would not be sold along with the other plants in the block. The plant was pinched back to make it break and force out new growth, and in due course, cuttings were taken from the white flowered shoots, rooted and ultimately moved to lining-out beds. Later still, these cuttings were potted and grown on for several months and then transferred to the cooler. After cooling for several weeks, the potted cuttings were removed from the cooler and forced into flower. Continued tests and observations confirmed that the characteristic white flowers of the new sport were fixed and established, and further asexual reproductions thereof by cuttings, as performed at Guthrie, Oklahoma, confirmed this feature was transmissible by asexual reproduction.

In addition to the white flowers of the new sport, as referred to above, it was found that it was endowed with other desirable improvements, which together, represent a unique combination which distinguishes the new sport from its parent variety, as well as from all other varieties of azaleas of which I am aware, as evidenced by the following characteristics which are outstanding in the new variety:

(1) A rapid and heavy habit of growth;

(2) Superior breaking habits, as compared with the parent variety "Gloria";

(3) A tendency to spread and form a larger head without developing the wild growth and bottom growth that are characteristic of the parent variety;

(4) Uniformity of branching habit;

(5) Evenness of bud setting; and (6) A distinctive and attractive almost pure white flower color, with only a slight pink cast in the half-open flowers which dissipates as the flowers become fully open.

The accompanying drawing shows a typical specimen plant of the new variety, as well as a typical specimen bloom thereof on a somewhat enlarged scale, all as depicted in color as nearly true as it is reasonably possible to make the same in a color illustration of this character.

The following is a detailed description of the new azalea variety, with color terminology in accordance with the Nickerson Color Fan, published by Munsell Color Company, Inc., of Baltimore, Maryland, except where general color terms of ordinary dictionary significances are obvious:

Locality where grown and observed: Guthrie, Oklahoma.

Propagation: Holds its distinguishing characteristics through succeeding propagations by cuttings.

Plant:

*Form.*—Dwarfish; much-branched; compact.

*Habit.*—Upright; branching.

*Rooting habit.*—Normal.

*Blooming habit.*—Tends to set buds evenly.

*Blooming season.*—Suitable for forcing during any season of the year under greenhouse conditions.

*Foliage.*—Size—from large to medium. Quantity—normal. Color: New foliage—upper side—Moderate Yellow Green, Plate 7.5GY 5/7; under side—Moderate Yellow Green, Plate 5GY 5/6. Old foliage—upper side—Dark Yellowish Green, Plate 2.5G 3/3; under side—Moderate Olive Green, Plate 7.5GY 4/4. Shape—ovate. Texture: Upper side—smooth; flat; under side—smooth. Margin—entire.

Flowers:

*Borne.*—In clusters of from 3 to 5 flowers to stem; on strong, long stems.

*Quantity.*—Abundant, in greenhouse.

*Continuity.*—One season lasting about 3 weeks.

*Size.*—Individual flowers average from about 2 inches to 2¾ inches in diameter.

*Petalage.*—Number of petals under normal conditions—usually 12. Color—white, with a pink cast in the half-open flowers, corresponding to Pale Purplish Pink, Plate 7.5RP 9/2, but fading to almost pure white over the entire petal as the flowers fully open. Texture—smooth. Appearance—double.

Bud: Color—Strong Yellow Green, Plate 5GY 6/8.

Reproductive organs:

*Stamens.*—Usually 8 in number. Color: Immature flower—Brilliant Greenish Yellow, Plate 7.5Y 9/8; mature flower—white.

*Pollen.*—Color—Brownish Orange, Plate 5YR 5/8.

*Styles (both immature and mature flower).*—Color—Strong Yellow Green, Plate 5GY 7/10.

*Ovaries (both immature and mature flower).*—Color—Strong Yellow Green, Plate 5GY 6/8.

General observations: The new variety is superior to the azalea variety known as "Alaska" (Plant Patent No. 147) in respect to its vigor, habit of growth, branching habit and uniformity of bud setting. Its branching habit is uniform over the entire plant, and after pinching, the new growths tend to develop at a uniform rate over the entire plant. The plant also tends to retain its leaves during the usual cooling period.

I claim:

A new and distinct variety of azalea plant, substantially as herein shown and described, characterized particularly as to novelty by the unique combination of a rapid and heavy habit of growth, superior breaking habits, as compared with the parent variety "Gloria," a tendency to spread and form a larger head without developing the wild growth and bottom growth that are characteristic of the parent variety, uniformity of branching habit, evenness of bud setting, and a distinctive and attractive almost pure white flower color, with only a slight pink cast in the half-open flowers which dissipates as the flowers become fully open.

No references cited.

ABRAHAM G. STONE, *Primary Examiner.*